United States Patent [19]
Longeron et al.

[11] Patent Number: 5,610,524
[45] Date of Patent: Mar. 11, 1997

[54] DEVICE FOR PETROPHYSICAL MEASUREMENT AND IMPLEMENTATION METHOD

[75] Inventors: Daniel Longeron, Sartrouville; Marc Fleury, La Celle Saint Cloud, both of France

[73] Assignee: Institut Francais du Petrole, Rueil Malmaison, France

[21] Appl. No.: 526,229

[22] Filed: Sep. 11, 1995

[30] Foreign Application Priority Data

Sep. 9, 1994 [FR] France .................. 94 10783

[51] Int. Cl.$^6$ .................................. G01V 3/02
[52] U.S. Cl. .................................. 324/376
[58] Field of Search .............. 324/376; 73/153, 73/38

[56] References Cited

U.S. PATENT DOCUMENTS

| | | | |
|---|---|---|---|
| 2,534,718 | 12/1950 | Leas et al. . | |
| 2,894,201 | 7/1959 | Piety | 324/376 |
| 3,302,101 | 1/1967 | Glanville | 324/376 |
| 4,490,676 | 12/1984 | Davis, Jr. et al. | 324/376 |
| 4,734,649 | 3/1988 | Barnaby . | |
| 4,907,448 | 3/1990 | Givens . | |
| 5,105,154 | 4/1992 | Givens et al. | 324/376 |
| 5,297,420 | 3/1994 | Gilliland . | |
| 5,493,226 | 2/1996 | Honarpoor et al. | 324/376 |

FOREIGN PATENT DOCUMENTS 2568373  1/1986  France .

*Primary Examiner*—Sandra L. O'Shea
*Assistant Examiner*—Roger C. Phillips
*Attorney, Agent, or Firm*—Antonelli, Terry, Stout & Kraus, LLP

[57] ABSTRACT

The device includes a cell for a sample, delimited lengthwise by two end pieces (7, 8) and laterally by a deformable sheath (17). The end pieces are traversed by channels (14) which place their grooved inside faces in communication respectively with two sources (14, 15) at an adjustable pressure delivering respectively a first and a second fluid. Between the inside faces of the end pieces and the sample, two semipermeable membranes (12, 13) are disposed, which are permeable respectively to the first and to the second fluid. Electrodes (18, 19) are placed inside sheath (17) in contact with the sample and connected to a system (24) for measuring the electrical conductivity of the sample. The cell is placed in a body (1) associated with pressure means (28) for applying a confinement pressure to sheath (17) and membranes (12, 13). The device is designed to operate at relatively high temperatures.

8 Claims, 4 Drawing Sheets

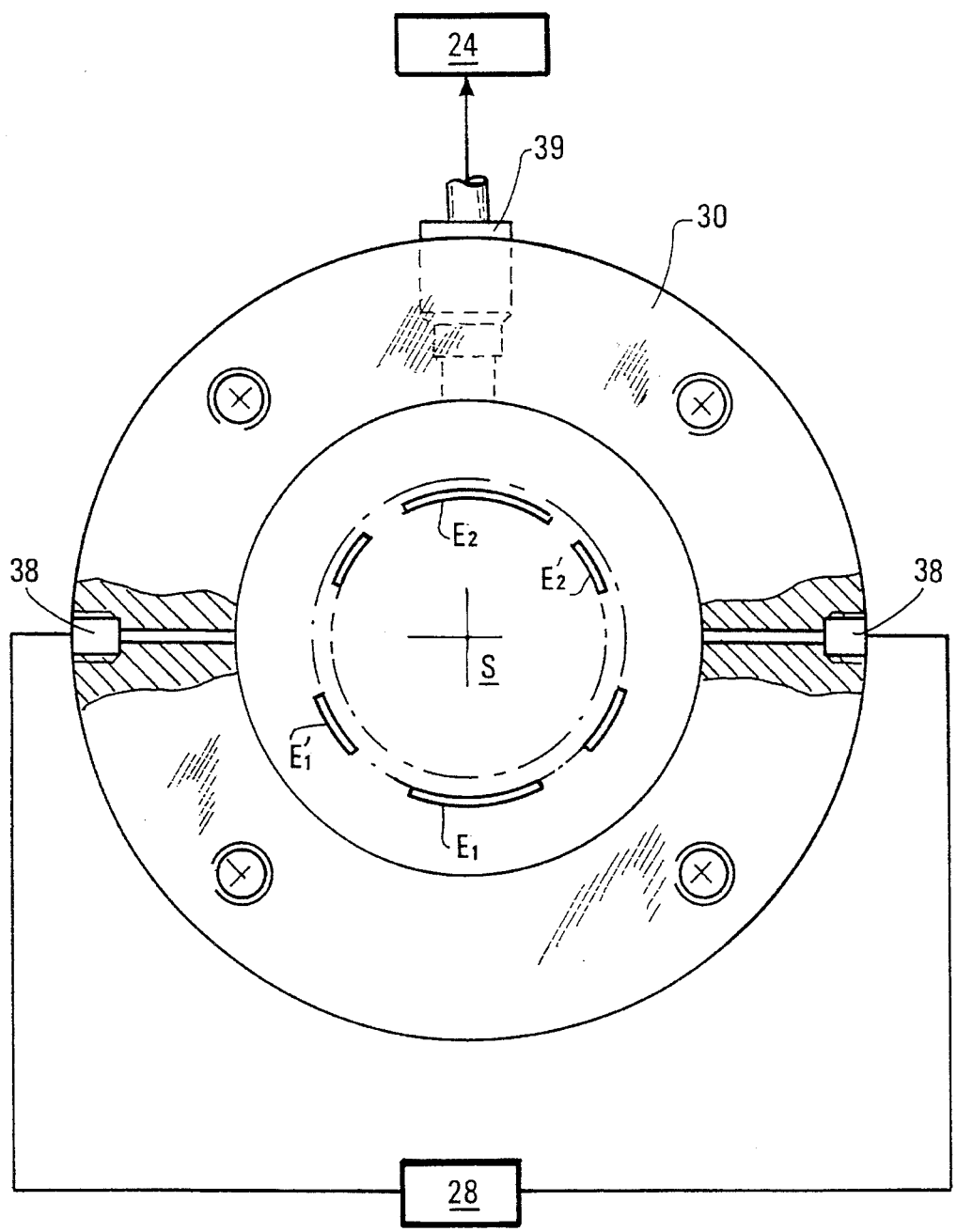

DEVICE FOR PETROPHYSICAL MEASUREMENT AND IMPLEMENTATION METHOD

FIELD OF THE INVENTION

The present invention relates to a device for making petrophysical measurements, allowing both the capillary pressure prevailing in a geological sample and its electrical conductivity to be measured. Such a tool is suitable for testing geological samples and determining various parameters such as the capillary pressure of rocks in drainage and soaking phases, their wettability indexes, their relative permeabilities, their resistivity indexes, etc.

The device has applications in particular in the petroleum field for testing rock samples from formations that contain or may contain petroleum effluents.

BACKGROUND OF THE INVENTION

It is important to determine the wettability of rocks with the water and oil that may be continued therein. For this purpose, the rock must be drained, namely fluids must be displaced to decrease the water saturation, then soaked, with the latter term signifying displacement of fluids allowing the water saturation (Sw) of the rock to be increased. The capillary pressure at a point is defined as the difference Pc in the equilibrium between the oil pressure Po and the water pressure Pwo This parameter makes sense only if the two fluids are in continuous phase in the porous medium. For a water-wettable medium, only positive values have a meaning. When the medium has mixed wettability, however, the fluids may remain in continuous phase for both positive and for negative capillary pressures (Pc).

For an application of this type, a complete capillary pressure measuring cycle must hence comprise (FIG. 1):

a) positive primary drainage of a sample initially 100% saturated with water (Curve 1);

b) positive soaking (curve 2);

c) negative soaking (curve 3);

d) negative drainage (curve 4); and e) positive secondary drainage (curve 5).

Knowledge of various parameters, particularly the wettability of the rocks, is useful particular when assisted recovery of a formation is to be carried out, draining the effluents it contains by injecting a fluid under pressure, after determining the fluid (water or gas) that is most appropriate for displacing the effluents.

The invention also has civil engineering applications for hydrology studies of the ground to determine its degree of pollution for example, and in building for testing construction materials in order in particular to make decisions on water-repellant treatments for example.

Measurement of the capillary pressure of rocks saturated with fluids by subjecting them to centrifugation at a progressive speed and measuring the quantity of fluid produced as a function of speed is known. The liquid-saturated sample is placed in an enclosure whose axis is in the direction of the centrifugal force and another fluid is injected to take the place of the expelled fluid as it is expelled. In the re-soaking phase, the speed is decreased in order to study the return of the original fluid to the sample. The pressure field created by centrifugation is expressed as a function of density r, radius R, and angular velocity w, y the relation: $\frac{1}{2}w^2.\Gamma(Rmax^2-R^2)$, for each fluid. The pressure of the two fluids at the sample outlet must be the same and must become zero at the outlet. Local saturations with this type of method are calculated by a negation program from the total quantity of water expelled from the sample. This method is implemented for example in patent applications FR-A-2,666,147 and EN.92/15215 by the applicant.

Another method, known as the "dynamic" method, consists of placing a sample in an elongate enclosure terminating at both its ends in water-permeable membranes. At one end, oil is injected under pressure into the enclosure. Water is also injected, but this injection is effected through the membrane and at a lower pressure. At the opposite end, the oil is evacuated directionally while the water leaves through the end membrane. By adjusting the oil and water injection rates, the capillary pressure is made to be the same at the inlet to the enclosure as at its outlet, which brings about uniform saturation that can be deduced from the fluid balance. The capillary pressure is obtained for example by measuring the difference between the oil and water pressures at the outlet of the enclosure. Such a method is described in particular by H. W. Brown in "Capillary Pressure Investigations," Petroleum Transactions AIME, Vol. 192, 1951.

U.S. Pat. No. 4,924,187 teaches a method for making wettability measurements on samples of porous rock in a confinement cell. The bar, of which the sample to be studied is composed, is placed inside an elongate deformable sheath associated with pressure means for applying a confinement pressure thereon laterally. At one end, the cell is closed by a porous membrane permeable to a first fluid such as brine saturating the bar but not to a second fluid such as oil or a gas. The porous membrane is made of a ceramic plate. This displacement fluid is injected under pressure at the opposite end of the cell and the first fluid, driven out of the sample, is collected at the first end. Between the conducting side pieces closing the cell at its two ends, an electrical voltage is applied. By means of electrodes that radially traverse the sheath and in contact with the sample at different locations along its length, the interelectrode electrical resistance and its variations are measured as the wetting fluid is drained from the bar.

SUMMARY OF THE INVENTION

The device according to the invention allows successive drainage and soaking phases to be effected on a porous solid sample wettable by at least a first fluid in order to determine physical parameters (particular petrophysical parameters): capillary pressures, water saturation (Sw), etc. of this sample. The device has a confinement cell having at least one deformable wall and means for applying a fluid under pressure to exert a given lateral pressure on the sample, two semipermeable membranes longitudinally delimiting the confinement cell, the first being wettable by a first conducting fluid and the second being wettable by a second fluid and nonwettable by the first fluid, and means for displacing the first and second fluids through the sample, in a first direction and in the direction opposite this first direction, as well as means for measuring the variations in interelectrode conductivity.

It is characterized by comprising at least one pair of electrodes disposed opposite each other according to at least one cross section of the cell, these electrodes being associated with the deformable wall and pressed strongly against the sample by application of the fluid under pressure.

The device has for example two coaxial side pieces between which the sample is disposed, the semipermeable membranes being disposed against the inside faces opposite each of these two side pieces. The deformable sheath is for example associated externally with these two side pieces.

The means for applying a fluid under pressure comprise an rigid external body in which the confinement cell is disposed, and means for connecting this chamber to an assembly delivering a fluid under pressure.

According to one embodiment, this body is delimited for example by a tubular element associated at its two opposite ends with two lateral flanges, each cooperating with one of the two side pieces.

According to another embodiment, the body is delimited by two sleeves pressed against each other through seals, these two sleeves each cooperating with one of the two side pieces, and the sample is placed inside an annular elastomer part forming the sheath.

The electrodes are connected for example to an instrument for measuring the conductivity outside the body through conductors leaving the body through fluidtight feedthroughs.

The means for achieving the displacements of fluids comprise for example a first source delivering the first fluid and a second source delivering the second fluid, and channels in the two side pieces for causing their inside faces which are respectively opposite the first source and the second source to communicate.

Preferably, the inside faces opposite the two side pieces are each provided with a network of grooves.

Each semipermeable membrane has for example a peripheral part designed to prevent any peripheral leakage of fluid.

According to one embodiment, the device has a plate provided with a perforated central part and a solid external part, which plate is disposed between each semipermeable membrane and the corresponding side piece, and seals for preventing fluid leaks from bypassing the membranes.

According to one particularly advantageous embodiment, the side pieces are dimensioned such as to confine a sample whose thickness is less than the cross section.

The device can also include a heat-regulated enclosure designed to contain the confinement cell.

According to another embodiment, the device has at least one first pair of electrodes for applying a differential potential and at least one second pair of electrodes for measuring the electrical current passing through the sample.

The method according to the invention is characterized by comprising confinement of the sample in a confinement cell delimited by a deformable sheath associated with means for applying fluid under pressure to exert a given confinement pressure on the sample, and two semipermeable membranes that are permeable respectively to a first fluid and to a second fluid, and displacing the fluids in the sample through two membranes, while measuring the variation in conductivity of the sample by means of electrodes disposed in contact with the sample, according to at least one cross section of the cell, and means for establishing an electrical field between the electrodes and for measuring the variations in interelectrode conductivity.

The device according to the invention considerably speeds up the rate of sample analysis without thereby altering the representativeness of the measurements made. This is due to the use of a cell designed for relatively thin samples, and membranes that are preferably microporous so that equilibrium status can be more rapidly attained at each pressure stage.

This is also due to the use of more enveloping electrodes facilitating better monitoring of the conductivity variations of the sample. Measurements of electrical conductivity of the sample as a function of saturation are particularly representative since the electrodes are pressed strongly against the sample. The enveloping form of the electrodes also allows a measurement that gives a good representation of the formation factor to be made.

BRIEF DESCRIPTION OF THE DRAWINGS

Nonlimiting examples of the device according to the invention will be described hereinbelow with reference to the attached drawings wherein:

FIG. 8 shows this second embodiment in cross section.

DETAILED DESCRIPTION OF THE INVENTION

Figure 1:
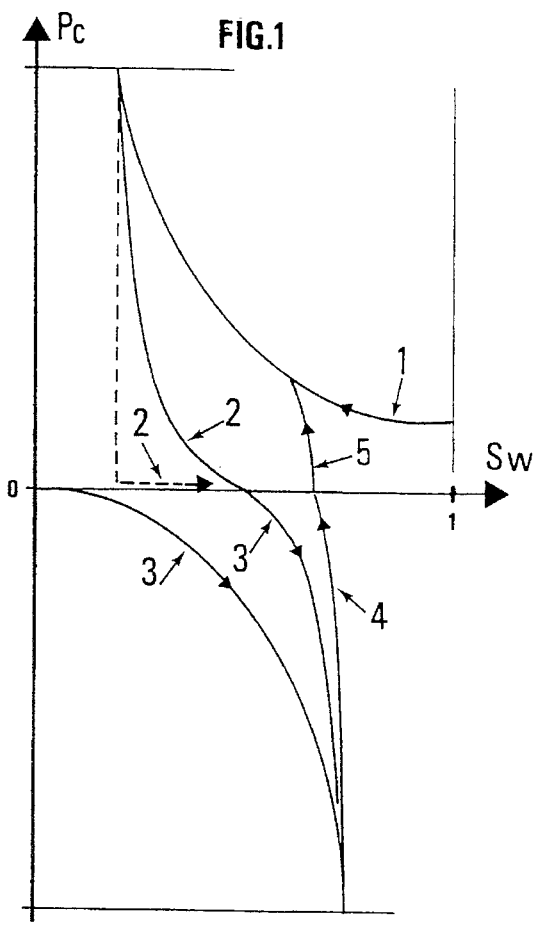
FIG. 1 shows indicatively the variations in capillary pressure in a sample during a complete drainage-soaking cycle.

Referring now generally to the Figures, the device according to the invention has a delimited hollow body 1 constituted of a cylindrical part 2 closed at its ends by two flanges 3, 4. Fastening means 5 and seals (not shown) enable the two flanges 3, 4 to be joined to cylindrical part 2.

Inside the body is a confinement cell 6 having two cylindrical side pieces 7, 8 provided externally with seals A which respectively engage openings 9 provided in the two flanges 3, 4 at their central axes. The sample to be studied is placed between them. The end faces opposite each of the two side pieces each have a network of grooves 11. Against the face of one of the side pieces is applied a first semipermeable membrane 12 permeable to a first fluid (a brine like that found in geological samples for example). Against the face of the other is applied another semipermeable membrane 13, permeable to a second fluid such as oil. It is preferable to use microporous partitions made for example by the companies Gore Tex, Sartorius, Poretics, Millipore, etc. Channels 14 pass through side piece 7 and allow the network of grooves 11 to communicate, at its end face, with a first source 15 delivering the first fluid under pressure. Likewise, channels 14 pass through side piece 8 bringing about communication with the network of grooves 11 corresponding to a second source 16 delivering the second fluid under pressure.

Figure 3:
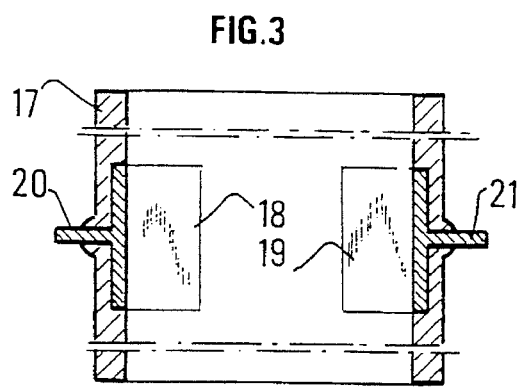
FIG. 3 shows the confinement sheath of the sample with the electrodes schematically in cross section.
Figure 4:
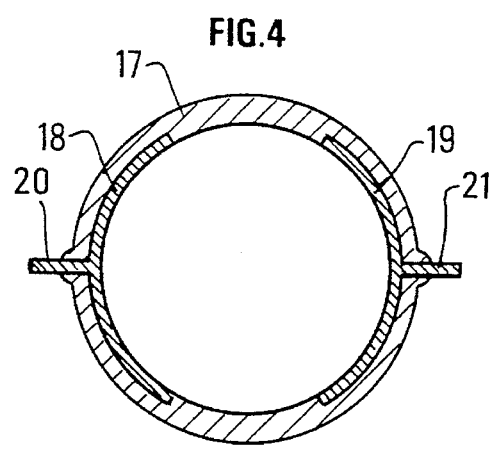
FIG. 4 shows the same confinement sheath schematically in cross section.
Figure 2:
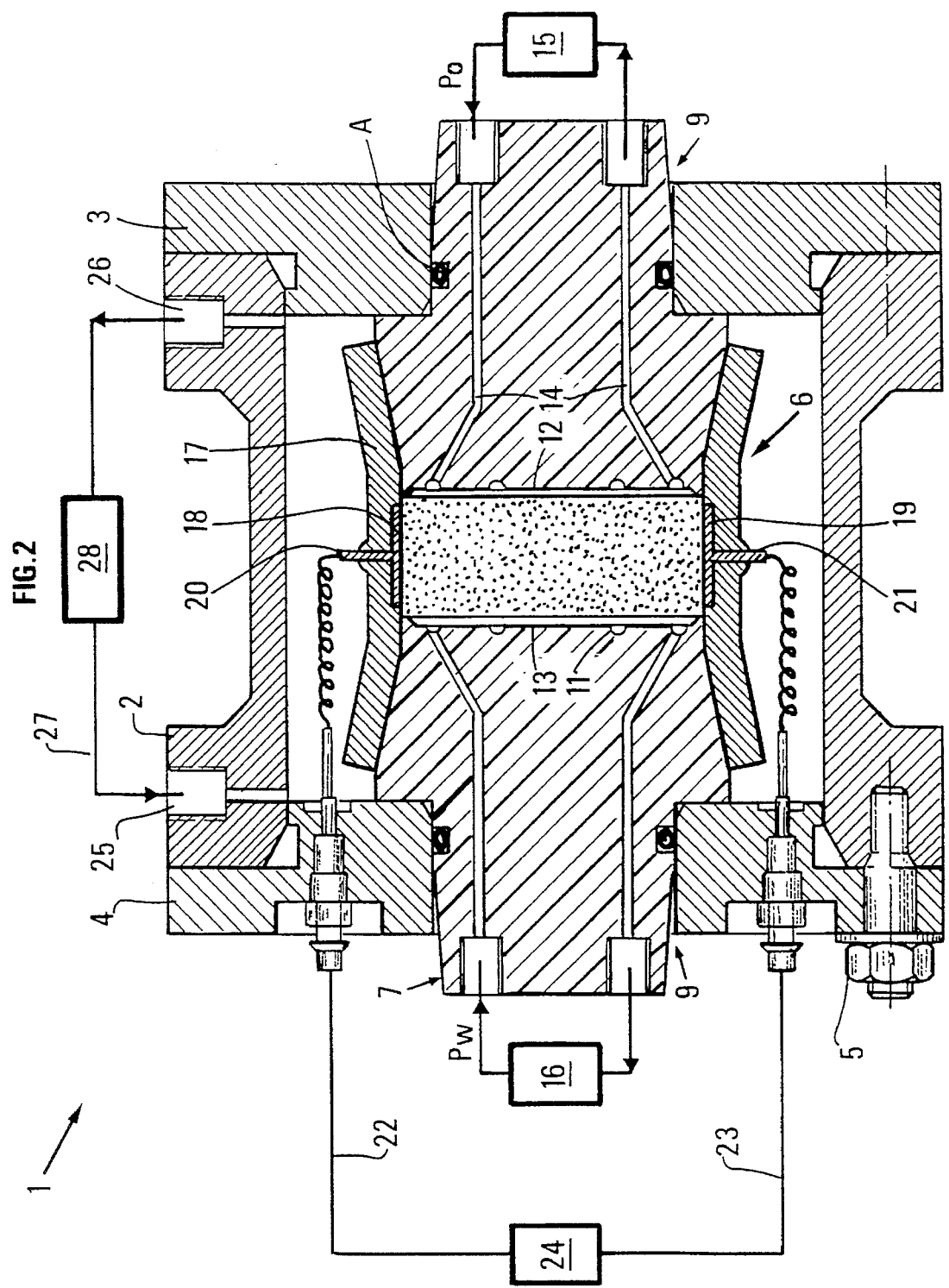
FIG. 2 shows a first embodiment of the device schematically in lengthwise section.

The part of each side piece 7, 8 inside the body is frustroconical for example. A flexible sheath 17 made of elastomer for example is threaded onto the frustroconical parts of the two side pieces to confine the space where the sample is located. In its center part (FIGS. 2, 3) the flexible sheath encloses two electrodes 18, 19, each having the shape of a portion of a circle, preferably disposed symmetrically relative to the sample and in electrical contact therewith. Each covers for example an angle of 120°. These two electrodes are connected to electrical conductors 20, 21 passing through flexible sheath 17. Through fluidtight feedthroughs 22, 23 they leave body 1 and are connected to an electrical conductivity measuring system 24 of a known type.

Cylindrical part 2 of the body communicates through openings 25, 26 and through a circuit 27 with a source 28 delivering a confinement fluid under pressure. Injection of this fluid has the effect of pressing sheath 17 and electrodes 18, 19 against the periphery of the sample thus reproducing the pressure to which it was subjected where it was sampled, in the subsoil for example.

Figure 5:
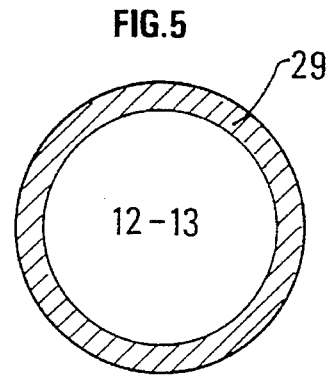
FIG. 5 shows schematically a microporous membrane with peripheral sealing means.

It is possible for example to use semipermeable membranes 12, 13 provided over their periphery (FIG. 5) with a reinforced, adhesive zone 29 so that they can be stuck to the periphery of the sample, avoiding any peripheral fluid leakage.

Figure 6:
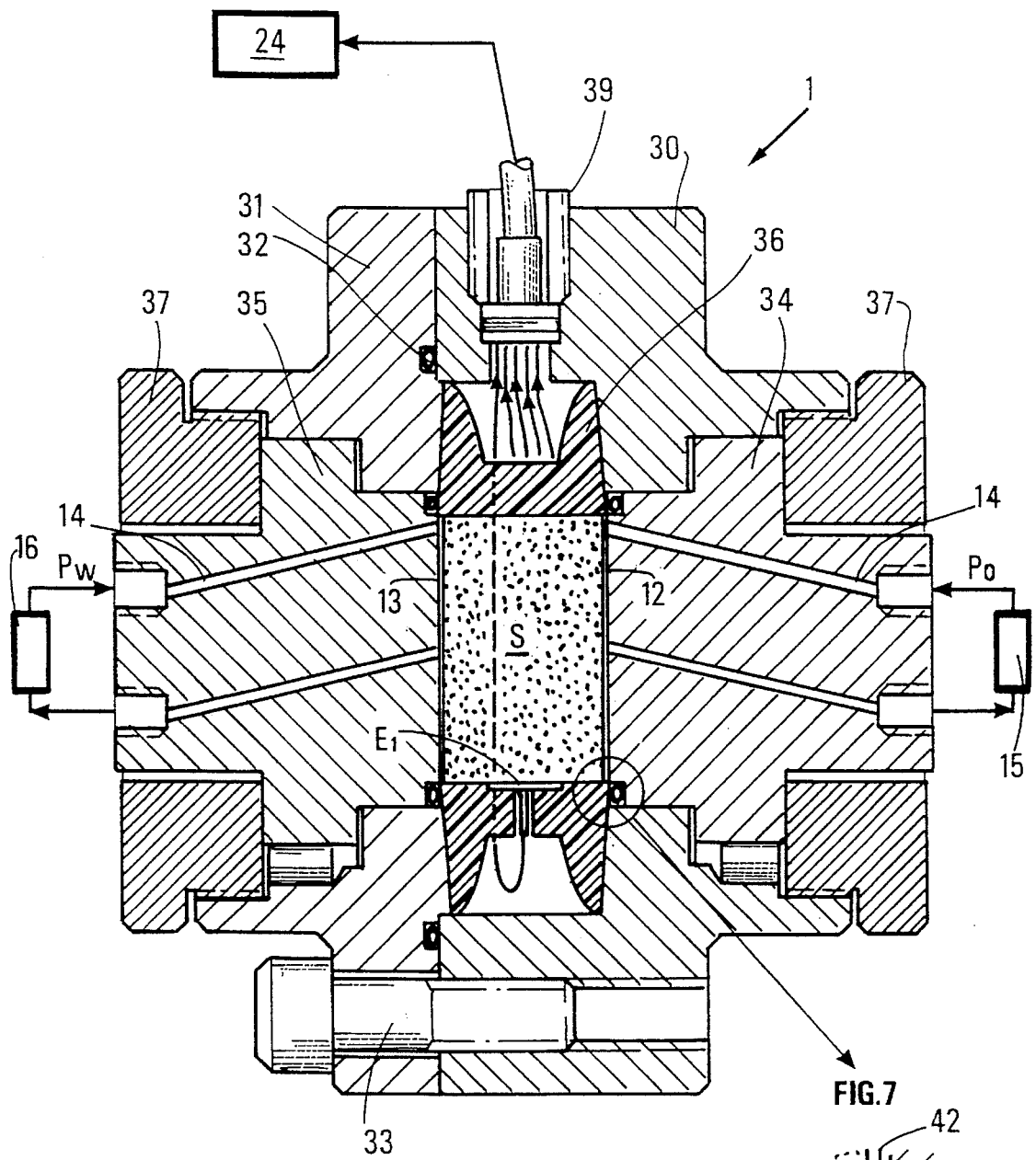
FIGS. 6 and 7 show schematically in lengthwise section a second embodiment of the device and a detail thereof.
Figure 7:
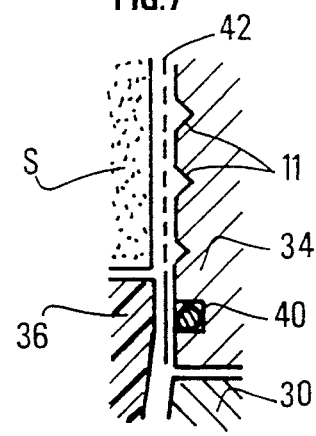

According to the embodiment of FIGS. 6 to 8, hollow body 1 is composed of two sleeves 30, 31 with cylindrical symmetry. They are applied against each other through seals 32 and connected by bolts 33. The two sleeves each have an axial cavity for a side piece 34, 35. Sample S is placed inside an elastomer annular part forming a sheath 36. Sample S with sheath 36 is installed in an interior cavity of sleeve 31 and delimited axially on either side by two side pieces 34, 35 and in contact with semipermeable membranes 12, 13. The two side pieces 34, 35 whose faces opposite each other are provided with grooves 11 are applied against the sample by screwing two nuts 37 into the two sleeves 30, 31. Radial orifices 38 through the outside wall of sleeve 30 (FIG. 8) allow an axial confinement pressure to be applied by pressure source 28.

The device has for example at least one first pair of electrodes E1, E2 disposed inside annular part 36, permitting application of an electrical current, and at least one second pair of electrodes E'1, E'2 between which the potential difference created in response to application of the electrical current is measured. This separate allocation of the pairs of electrodes, one for application of a current and the other for measuring differences in potential avoids contact resistances. If several pairs of electrodes such as E'1, E'2 are available, the corresponding electrodes of these pairs are interconnected.

Through a stopper 39 provided with a fluidtight feedthrough, wires connected to the various electrodes are connected to electrical conductivity measurement system 24.

To achieve perfect fluidtightness of the confinement enclosure of sample S, each side piece 34, 35 has (FIG. 7 a groove in its end wall for a seal 40, and between each of membranes 12, 13 and corresponding side piece 34, 35 is interposed a metal grid 42 covered with a plastic coating. This grid is provided at its periphery with a nonperforated crown which prevents any fluid leakage from bypassing membranes 12, 13.

Both the embodiments described can be placed in a heat-regulated enclosure (not shown) designed to reproduce the temperature of the geological formation from which the sample was extracted.

OPERATION

A porous sample saturated with a first fluid such as a brine is placed between the sleeves with semipermeable membranes 12, 13 on either side. The sheath is placed around the two sleeves to form the confinement cell. Body 1 is then enclosed around the cell in a fluidtight fashion and a confinement pressure is applied to the sample by means of pressurized fluid source 28.

By means of fluid source 16, first circulation of a second fluid is established in the circuit composed of channels 14 and network of grooves 11 of side piece 7 or 35 in order to distribute it well over the entire anterior face of semipermeable membrane 13. The same is done with source 15 to establish continuity of the first fluid in channels 14 of the other side piece 8 or 34 and in contact with the other semipermeable membrane 12.

With the circulation pressure Po of the first fluid imposed by source 15 remaining constant, the pressure of the second fluid Pw is increased up to a first plateau. It penetrates the sample through membrane 13, and the first fluid driven outside the sample, having traversed the other membrane 12, is collected in the opposite circuit. The quantity of water thus expelled is measured and in system 24, the variation in electrical conductivity produced by displacement of fluids inside the sample is also recorded in system 24.

In successive stages, displacement pressure Po is increased, recording the quantities of water expelled as well as the resulting variations in the conductivity of the bar. Drainage continues until a maximum pressure value is reached. One may then plot a curve representing the variations in saturation Sw of the sample as a function of the capillary pressure imposed (curve 1 of FIG. 1 for example).

The symmetrical arrangement of the device lends itself similarly to sample resoaking operations. A drop in the oil pressure Po and a correlative increase in water pressure Po have the effect of displacing the two fluids inside the sample in the reverse direction, with the water flowing back into the pores of the rock through wettable membrane 12, and the displacement fluid returning to the circuit in side piece 7 or 35 through microporous membrane 13. Also, measurements of variations in electrical conductivity resulting from these fluid displacements are continuously made.

By successive drainage and resoaking cycles, all the variation curves in FIG. 1 can be plotted.

We claim:

1. A device for producing, in a porous solid sample having a lateral surface and being wettable by at least a first fluid, drainage and soaking phases in order to determine physical parameters of the sample, said device comprising a confinement cell for the sample delimited by a deformable cylindrical sheath having an inner wall, and two opposite end elements; fluid pressure means communicating with opposite ends of the sample through said end elements, for displacing said first fluid and a second fluid through the sample in a first longitudinal direction and in a direction opposite to the first longitudinal direction, respectively; two semipermeable membranes interposed between the sample and, respectively, the two end elements, the first membrane being wettable with the first fluid, the second membrane being wettable by the second fluid and nonwettable by the first fluid; measuring means for measuring electrical conductivity of the sample; and pressure means for laterally pressing the sheath against the sample; said device further comprising at least one pair of conductive plates connected with said measuring means, said plates being associated with the inner wall of the sheath and being shaped, respectively, to conform to substantial opposite portions of the lateral surface of the sample.

2. A device according to claim 1, wherein said at least one pair of conductive plates comprises at least two pair of conductive plates in close contact with the lateral wall of the sample, a first pair of plates being electrically connected with a voltage generating means, a second pair of said plates being connected with a current measuring means, the at least two pair of plates being positioned transversely to a given cross sectional portion of the sample.

3. A device as claimed in claim 1, wherein each of said semipermeable membranes is provided with a peripheral part that is sealed to the lateral surface of the sample, whereby peripheral leakage of fluid from the sample is prevented.

4. A device according to claim 1 further including perforated plates provided with a peripheral non-peripheral portion positioned between each end element of the confinement cell and a corresponding semipermeable membrane, each of said end elements being provided with a tight seal for being pressed on said peripheral non-peripheral portion, whereby fluid leakage from the sample is prevented.

5. A device according to claim 1, wherein the pressure means comprises a rigid external body in which a confinement cell is positioned, and means for connecting said body to an assembly for delivering a fluid under pressure into said body.

6. A device according to claim 5, wherein the rigid body is defined by a tubular element associated at its opposite ends with two lateral flanges, each flange cooperating with one of the two end elements.

7. A device according to claim 5, wherein the rigid body is defined by two sleeves pressed against each other through seals, said two sleeves each cooperating with one of the two end elements, said sheath comprising an annular elastomeric element in which the sample is positioned.

8. A device according to claim 1, wherein the measuring means are connected to the at least one pair of conductive plates through conductors passing from a rigid body surrounding the confinement cell through fluid tight-feed through connections.

* * * * *